(12) United States Patent
Hori et al.

(10) Patent No.: US 8,846,983 B2
(45) Date of Patent: Sep. 30, 2014

(54) METHOD FOR REDUCING HALOGENOBENZOIC ACID ESTER USING RUTHENIUM CARBONYL COMPLEX

(71) Applicant: Takasago International Corporation, Tokyo (JP)

(72) Inventors: Kiyoto Hori, Koza-gun (JP); Osamu Ogata, Hiratsuka (JP); Wataru Kuriyama, Ota-ku (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 14/100,163

(22) Filed: Dec. 9, 2013

(65) Prior Publication Data
US 2014/0163257 A1   Jun. 12, 2014

(30) Foreign Application Priority Data
Dec. 12, 2012 (JP) ................. 2012-270942

(51) Int. Cl.
*C07C 29/149* (2006.01)
*C07C 51/60* (2006.01)

(52) U.S. Cl.
CPC ..................... *C07C 51/60* (2013.01)
USPC ...................................................... 568/814

(58) Field of Classification Search
None
See application file for complete search history.

(56) References Cited

U.S. PATENT DOCUMENTS 8,471,048 B2 * 6/2013 Kuriyama et al. ............... 556/8
2011/0237814 A1 * 9/2011 Kuriyama et al. ............... 556/8

OTHER PUBLICATIONS

Ian Carpenter, et al., "Convenient and improved protocols for the hydrogenation of esters using Ru catalysts derived from (P,P), (P,N,N) and (P,N,O) ligands", Dalton Transactions, 2012, pp. 10136-10140, vol. 41.

* cited by examiner

*Primary Examiner* — Brian J Davis
(74) *Attorney, Agent, or Firm* — Sughrue Mion, PLLC

(57) ABSTRACT

An object of the present invention is to provide a method for reducing a halogenobenzoic acid ester, in which dehalogenation is inhibited, by using a readily available catalyst. The method comprises reducing an ester with hydrogen gas by using an aromatic hydrocarbon as a solvent in the presence of a ruthenium complex represented by the following general formula (1):

$$RuXY(CO)(L) \qquad (1)$$

where X and Y represent monovalent anionic ligands, and L represents a tridentate aminodiphosphine ligand represented by the following general formula (2):

where $R^{Z1}$ represents an alkyl group having 1 to 4 carbon atoms, each $R^{Z2}$ represents an alkyl group having 1 to 4 carbon atoms or a halogen atom, any adjacent two $R^{Z2}$s may form a ring, Hal represents a halogen atom, and n represents 0 to 4.

4 Claims, No Drawings

METHOD FOR REDUCING HALOGENOBENZOIC ACID ESTER USING RUTHENIUM CARBONYL COMPLEX

CROSS REFERENCE TO RELATED APPLICATIONS

This application is claims benefit of priority based on Japanese Patent Application No. 2012-270942, filed Dec. 12, 2012, the content of which is incorporated herein by reference in its entirety.

TECHNICAL FIELD

The present invention relates to a method for reducing a halogenobenzoic acid ester.

BACKGROUND ART

Dehalogenation is known to occur in production of a halogenobenzyl alcohol by reduction of a halogenobenzoic acid ester with hydrogen gas using a transition metal complex as a catalyst, but there are only a few reports on reduction of halogenobenzoic acid esters. Dalton Trans., 2012, 41, 10136 reports reduction of methyl halogenobenzoates, in which dehalogenation is inhibited, using a ruthenium complex having a PNN pincer-type ligand or the like. However, this reduction has such a problem that since the reaction temperature has to be low, further improvement in the catalyst ratio cannot be expected.

SUMMARY OF INVENTION

Technical Problems

An object of the present invention is to provide a method for reducing a halogenobenzoic acid ester, in which dehalogenation is inhibited, by using a ruthenium complex which is readily available as a commercial product or the like.

Solution to Problems

Specifically, the present invention includes the following contents [1] to [3].

[1] A reduction method, in which dehalogenation is inhibited, the method comprising reducing a halogenobenzoic acid ester in an aromatic hydrocarbon solvent in the presence of a ruthenium complex to thereby produce an alcohol compound, the ruthenium complex being represented by the following general formula (1):

$$\text{RuXY(CO)(L)} \tag{1},$$

wherein X and Y, which may be the same or different, each represent a monovalent anionic ligand, and L represents a tridentate aminodiphosphine ligand represented by the following general formula (2):

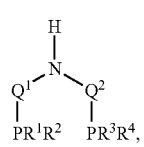

(2)

wherein $R^1$, $R^2$, $R^3$, and $R^4$, which may be the same or different, each represent a hydrogen atom, an alkyl group, a cycloalkyl group, an aryl group, an aralkyl group, an alkoxy group, a cycloalkyloxy group, an aryloxy group, an aralkyloxy group, a heterocyclic group, or a substituted amino group, each of the pair of $R^1$ and $R^2$ and the pair of $R^3$ and $R^4$ may be bonded to each other to form a ring together with the corresponding adjacent phosphorus atom, and the alkyl group, the cycloalkyl group, the aryl group, the aralkyl group, the alkoxy group, the cycloalkyloxy group, the aryloxy group, the aralkyloxy group, and the heterocyclic group are optionally substituted, and $Q^1$ and $Q^2$, which may be the same or different, each represent an optionally substituted divalent alkylene group, an optionally substituted divalent cycloalkylene group, or an optionally substituted divalent aralkylene group, the halogenobenzoic acid ester being represented by the following general formula (6):

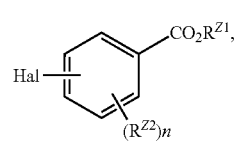

(6)

wherein $R^{Z1}$ represents an alkyl group having 1 to 4 carbon atoms, each $R^{Z2}$ represents an alkyl group having 1 to 4 carbon atoms or a halogen atom, or any adjacent two $R^{Z2}$s may form a ring, Hal represents a halogen atom, and n represents 0 to 4, the alcohol compound being represented by the following general formula (7):

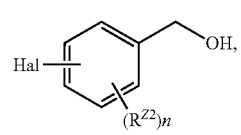

(7)

wherein each $R^{Z2}$ represents an alkyl group having 1 to 4 carbon atoms or a halogen atom, or any adjacent two $R^{Z2}$s may form a ring, Hal represents a halogen atom, and n represents 0 to 4.

[2] The reduction method according to [1], wherein the substitution position of the Hal in general formulae (6) and (7) is para to the alkoxycarbonyl group and the hydroxymethyl group.

[3] The reduction method according to [1] or [2], wherein the aromatic hydrocarbon solvent is selected from toluene, xylene, and mesitylene.

Effects of the Invention

The present invention provides a method for reducing a halogenobenzoic acid ester, in which dehalogenation is inhibited, using a readily available catalyst.

DESCRIPTION OF EMBODIMENTS

First, the ruthenium carbonyl complex of the present invention represented by general formula (1) will be described.

The tridentate aminodiphosphine ligand represented by L in general formula (1) includes those having two phosphino groups and a —NH— group. The tridentate aminodiphosphine ligand specifically includes those represented by the above-described general formula (2).

$R^1$, $R^2$, $R^3$, and $R^4$ in the tridentate aminodiphosphine ligand represented by general formula (2) will be described.

$R^1$, $R^2$, $R^3$, and $R^4$, which may be the same or different, each represent a hydrogen atom, an alkyl group, a cycloalkyl group, an aryl group, an aralkyl group, an alkoxy group, a cycloalkyloxy group, an aryloxy group, an aralkyloxy group, a heterocyclic group, or a substituted amino group, each of the pair of $R^1$ and $R^2$ and the pair of $R^3$ and $R^4$ may be bonded to each other to form a ring together with the corresponding adjacent phosphorus atom, and the alkyl group, the cycloalkyl group, the aryl group, the aralkyl group, the alkoxy group, the cycloalkyloxy group, the aryloxy group, the aralkyloxy group, and the heterocyclic group are optionally substituted. In the substituted amino group, each group of atoms introduced as a substituent to the amino group may be further substituted.

The alkyl group includes linear or branched alkyl groups having 1 to 50 carbon atoms, preferably 1 to 20 carbon atoms, and more preferably 1 to 10 carbon atoms. Examples of the alkyl groups include a methyl group, an ethyl group, a n-propyl group, an isopropyl group, a n-butyl group, an isobutyl group, a s-butyl group, a tert-butyl group, a n-pentyl group, a n-hexyl group, a n-octyl group, and the like.

The cycloalkyl group includes monocyclic, polycyclic, or fused cyclic cycloalkyl groups having 3 to 30 carbon atoms, preferably 3 to 20 carbon atoms, and more preferably 3 to 10 carbon atoms. Examples of the cycloalkyl groups include a cyclopropyl group, a cyclopentyl group, a cyclohexyl group, and the like.

The aryl group includes monocyclic, polycyclic, or fused cyclic aryl groups having 6 to 36 carbon atoms, preferably 6 to 18 carbon atoms, and more preferably 6 to 14 carbon atoms. Specific examples of the aryl groups include a phenyl group, a naphthyl group, an anthryl group, a phenanthryl group, a biphenyl group, and the like.

The aralkyl group includes groups which are the same as the above-described alkyl groups, except that at least one hydrogen atom thereof is substituted with any one of the above-described aryl groups. For example, aralkyl groups having 7 to 15 carbon atoms are preferable, and specific examples thereof include a benzyl group, a 1-phenylethyl group, a 2-phenylethyl group, a 1-phenylpropyl group, a 3-naphthylpropyl group, and the like.

The alkoxy group includes alkoxy groups each having a linear or branched alkyl group having 1 to 20 carbon atoms, preferably 1 to 15 carbon atoms, and more preferably 1 to 10 carbon atoms. Examples of the alkoxy groups include a methoxy group, an ethoxy group, a n-propoxy group, an isopropoxy group, a n-butoxy group, an isobutoxy group, a s-butoxy group, a tert-butoxy group, a n-pentyloxy group, and the like.

The cycloalkyloxy group includes cycloalkyloxy groups each having, as a part of the group, a monocyclic, polycyclic, or fused cyclic cycloalkyl group having 3 to 20 carbon atoms, preferably 3 to 15 carbon atoms, and more preferably 3 to 10 carbon atoms. Examples of the cycloalkyloxy groups include a cyclopropyloxy group, a cyclopentyloxy group, a cyclohexyloxy group, and the like.

The aryloxy group includes aryloxy groups each having a monocyclic, polycyclic, or fused cyclic aryl group having 6 to 36 carbon atoms, preferably 6 to 18 carbon atoms, and more preferably 6 to 14 carbon atoms. Specific examples of the aryloxy groups include a phenoxy group, a tolyloxy group, a xylyloxy group, a naphthoxy group, and the like.

The aralkyloxy group includes groups which are the same as the above-described alkoxy groups or the above-described cycloalkyloxy groups, except that at least one hydrogen atom of each of the alkyl groups described for the alkoxy groups and the cycloalkyl groups described for the cycloalkyloxy groups is substituted with any one of the above-described aryl groups. For example, aralkyloxy groups having 7 to 15 carbon atoms are preferable, and specific examples thereof include a benzyloxy group, a 1-phenylethoxy group, a 2-phenylethoxy group, a 1-phenylpropoxy group, a 2-phenylpropoxy group, a 3-phenylpropoxy group, a 4-phenylbutoxy group, a 1-naphthylmethoxy group, a 2-naphthylmethoxy group, and the like.

The heterocyclic group includes aliphatic heterocyclic groups and aromatic heterocyclic groups. Examples of the aliphatic heterocyclic groups include 3- to 8-membered and preferably 4- to 6-membered monocyclic aliphatic heterocyclic groups each having 2 to 14 carbon atoms and containing at least one and preferably 1 to 3 heteroatoms such as nitrogen atoms, oxygen atoms and/or sulfur atoms; and polycyclic or fused cyclic aliphatic heterocyclic groups each having the 3- to 8-membered and preferably 4- to 6-membered ring as a constituent. Specific examples of the aliphatic heterocyclic groups include an azetidyl group, a azetidino group, a pyrrolidyl group, a pyrrolidino group, a piperidinyl group, a piperidino group, a piperazinyl group, a piperazino group, a morpholinyl group, a morpholino group, a tetrahydrofuryl group, a tetrahydropyranyl group, a tetrahydrothiophenyl group, and the like.

Examples of the aromatic heterocyclic groups include 5 or 6-membered monocyclic heteroaryl groups each having 2 to 15 carbon atoms and containing at least one and preferably 1 to 3 heteroatoms such as nitrogen atoms, oxygen atoms and/or sulfur atoms; and polycyclic or fused cyclic heteroaryl groups each having the 5 or 6-membered ring as a constituent. Specific examples of the aromatic heterocyclic groups include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthyridyl group, a cinnolyl group, a benzoimidazolyl group, a benzoxazolyl group, a benzothiazolyl group, an acridyl group, an acridinyl group, and the like.

The substituted amino group is preferably a disubstituted amino group, which includes amino groups in each of which two hydrogen atoms of the amino group are substituted with the same or different ones of the above-described alkyl groups, cycloalkyl groups, aryl groups, aralkyl groups, and heterocyclic groups. Specifically, the disubstituted amino group includes dialkylamino groups such as an N,N-diethylamino group and an N,N-diisopropylamino group; dicycloalkylamino groups such as an N,N-dicyclohexylamino group; diarylamino groups such as an N,N-diphenylamino group and an N-naphthyl-N-phenylamino group; diaralkylamino groups such as an N,N-dibenzylamino group; and the like.

The substituents which may be possessed by the alkyl groups, the cycloalkyl groups, the aryl groups, the aralkyl groups, the alkoxy groups, the cycloalkyloxy groups, the aryloxy groups, the aralkyloxy groups, and the heterocyclic groups, and by the alkyl groups, cycloalkyl groups, aryl groups, aralkyl groups, and the heterocyclic groups on the substituted amino groups include the alkyl groups, cycloalkyl groups, aryl groups, aralkyl groups, alkoxy groups, cycloalkyloxy groups, aryloxy groups, aralkyloxy groups, heterocyclic groups, and substituted amino groups, which are described above for $R^1$, $R^2$, $R^3$, and $R^4$; halogen atoms; silyl groups; optionally protected hydroxy groups, and the like.

The halogen atoms as substituents in $R^1$, $R^2$, $R^3$, and $R^4$ include a fluorine atom, a chlorine atom, a bromine atom, and an iodine atom.

The silyl groups as substituents in $R^1$, $R^2$, $R^3$, and $R^4$ include those in which three hydrogen atoms of a silyl group are each substituted with any one of the alkyl groups, cycloalkyl groups, aryl groups, and aralkyl groups, which are described above for $R^1$, $R^2$, $R^3$, and $R^4$; and the like. Specifically, the silyl groups include a trimethylsilyl group, a triethylsilyl group, a t-butyldimethylsilyl group, a t-butyldiphenylsilyl group, a triphenylsilyl group, and the like.

The optionally protected hydroxy groups as substituents in $R^1$, $R^2$, $R^3$, and $R^4$ include an unprotected hydroxy group; hydroxy groups optionally protected with common hydroxy group-protecting groups such as silyl groups (including a trimethylsilyl group, a tert-butyldimethylsilyl group, and a tert-butyldiphenylsilyl group), a benzyl group, and a methoxymethyl group; and the like.

Each of the pair of $R^1$ and $R^2$ and the pair of $R^3$ and $R^4$ may be bonded to each other to form a ring together with the corresponding adjacent phosphorus atom. The ring formed includes four-membered rings, five-membered rings, and six-membered rings. Specifically, the rings include a phosphetane ring, a phospholane ring, a phosphinane ring, a 2,4-dimethylphosphetane ring, a 2,4-diethylphosphetane ring, a 2,5-dimethylphospholane ring, a 2,5-diethyl phospholane ring, a 2,6-dimethylphosphinane ring, a 2,6-diethylphosphinane ring, and the like.

$Q^1$ and $Q^2$ in general formula (2) will be described.

The divalent alkylene group includes linear or branched divalent alkyl chains having 1 to 20 carbon atoms, preferably 1 to 10 carbon atoms, and more preferably 1 to 6 carbon atoms, and specific examples thereof include a methylene group, an ethylene group, a trimethylene group, a tetramethylene group, a pentamethylene group, and the like.

The divalent cycloalkylene group includes divalent groups derived from monocyclic, polycyclic, or fused cyclic cycloalkyl groups having 3 to 15 carbon atoms, preferably 3 to 10 carbon atoms, and more preferably 3 to 6 carbon atoms, and examples thereof include a cyclopropylene group, a cyclobutylene group, a cyclopentylene group, a cyclohexylene group, and the like.

The divalent aralkylene group includes divalent groups which has 7 to 11 carbon atoms and which are the same as aralkyl groups such as a benzyl group and a phenethyl group, except that one hydrogen atom is removed from the aryl group in each of the aralkyl groups. The divalent aralkylene group includes a benzylene group (-Ph-$CH_2$—), a 2-phenylethylene group (-Ph-$CH_2CH_2$—), a 1-naphthylmethylene group (—Np—$CH_2$—), a 2-naphthylmethylene group (—Np—$CH_2$—), and the like, where -Ph- represents a phenylene group, and —Np— represents a naphthylene group.

The substituents which may be possessed by these divalent alkylene groups, divalent cycloalkylene groups, and divalent aralkylene groups include the alkyl groups, cycloalkyl groups, aryl groups, aralkyl groups, alkoxy groups, cycloalkyloxy groups, aryloxy groups, aralkyloxy groups, heterocyclic groups, halogen atoms, silyl groups, substituted amino groups, and optionally protected hydroxy groups, which are described above for $R^1$, $R^2$, $R^3$, and $R^4$ in general formula (2), and the like.

Next, the monovalent anionic ligand represented by X or Y in general formula (1) will be described.

Examples of the monovalent anionic ligand include hydride, alkoxy groups, cycloalkyloxy groups, aryloxy groups, aralkyloxy groups, a hydroxy group, acyloxy groups, sulfonyloxy groups, halogen ions, $AlH_4^-$, $AlH_2(OCH_2CH_2OCH_3)_2^-$, $BH_4^-$, $BH_3CN^-$, $BH(Et)_3^-$, $BH(sec-Bu)_3^-$, and the like. Preferred are $BH_4^-$, hydride, and a chlorine ion. It is preferable that one of X and Y be hydride, and the other be a chlorine ion. Note that, in this description, the hydride is also simply referred to as hydrogen, and the halogen ion is also simply referred to as halogen, in some cases.

The alkoxy groups, the cycloalkyloxy groups, the aryloxy groups, and the aralkyloxy groups include the above-described groups described for the general formula (2).

The acyloxy groups include those represented by $R^aCO_2$. $R^a$ in the acyloxy group $R^aCO_2$ may be a hydrogen atom, an alkyl group, a cycloalkyl group, an aryl group, or an aralkyl group. Examples of the alkyl group, the cycloalkyl group, the aryl group, and the aralkyl group include the alkyl groups, cycloalkyl groups, aryl groups, and aralkyl groups, which are described above for $R^1$, $R^2$, $R^3$, and $R^4$ in general formula (2). These alkyl groups, cycloalkyl groups, aryl groups, and aralkyl groups may be further substituted with any of the alkyl groups, cycloalkyl groups, aryl groups, aralkyl groups, alkoxy groups, cycloalkyloxy groups, aralkyloxy groups, aryloxy groups, heterocyclic groups, halogen atoms, silyl groups, and optionally protected hydroxy groups, which are described above for $R^1$, $R^2$, $R^3$, and $R^4$ in general formula (2); optionally protected amino groups described below; and the like.

The optionally protected amino groups as the substituents in $R^a$ include an unprotected amino group; monoalkylamino or dialkylamino groups such as an N-methylamino group, an N,N-dimethylamino group, an N,N-diethylamino group, an N,N-diisopropylamino group, and an N-cyclohexylamino group; monoarylamino or diarylamino groups such as an N-phenylamino group, an N,N-diphenylamino group, an N-naphthylamino group, and an N-naphthyl-N-phenylamino group; monoaralkylamino or diaralkylamino groups such as an N-benzylamino group and an N,N-dibenzylamino group; acylamino groups such as a formylamino group, an acetylamino group, a propionylamino group, a pivaloylamino group, a pentanoylamino group, a hexanoylamino group, and a benzoylamino group; alkoxycarbonylamino groups such as a methoxycarbonylamino group, an ethoxycarbonylamino group, a n-propoxycarbonylamino group, a n-butoxycarbonylamino group, a tert-butoxycarbonylamino group, a pentyloxycarbonylamino group, and a hexyloxycarbonylamino group; aryloxycarbonylamino groups such as a phenyloxycarbonylamino group; aralkyloxycarbonylamino groups such as a benzyloxycarbonylamino group; and the like. Examples of the optionally protected amino groups further include amino groups protected with common amino group-protecting groups used for peptide synthesis and the like.

Examples of $R^a$ include a methyl group, an ethyl group, a propyl group, a tert-butyl group, a trifluoromethyl group, a phenyl group, a pentafluorophenyl group, and the like.

The sulfonyloxy groups include those represented by $(R^SSO_3)$. $R^S$ in the sulfonyloxy group $R^SSO_3$ may be the same as described for $R^a$ in the acyloxy group.

The halogen ions include a fluorine ion, a chlorine ion, a bromine ion, and an iodine ion. Preferred are a chlorine ion and a bromine ion, and further preferred is a chlorine ion.

Preferred tridentate aminodiphosphine ligands are those represented by the following general formula (3):

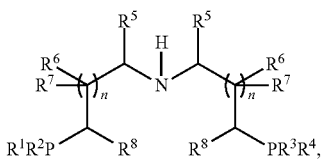

(3)

wherein $R^1$, $R^2$, $R^3$, and $R^4$, which may be the same or different, each represent a hydrogen atom, an alkyl group, a cycloalkyl group, an aryl group, an aralkyl group, an alkoxy group, a cycloalkyloxy group, an aryloxy group, an aralkyloxy group, a heterocyclic group, or a substituted amino group, each of the pair of $R^1$ and $R^2$ and the pair of $R^3$ and $R^4$ may be bonded to each other to form a ring together with the corresponding adjacent phosphorus atom, and the alkyl group, the cycloalkyl group, the aryl group, the aralkyl group, the alkoxy group, the cycloalkyloxy group, the aryloxy group, the aralkyloxy group, and the heterocyclic group are optionally substituted, $R^5$, $R^6$, $R^7$, and $R^8$, which may be the same or different, each represent a hydrogen atom, an alkyl group, a cycloalkyl group, an aryl group, or an aralkyl group, each of the pair of $R^5$s, the pairs of $R^5$ with $R^6$, $R^7$, or $R^8$, the pairs of $R^6$ with $R^7$ or $R^8$ may be bonded to each other to form a ring together with the corresponding adjacent carbon atom(s), n represents an integer of 0 to 3, and the alkyl group, the cycloalkyl group, the aryl group, and the aralkyl group are optionally substituted.

The alkyl group, the cycloalkyl group, the aryl group, and the aralkyl group represented by $R^5$, $R^6$, $R^7$, or $R^8$ in general formula (3) include the alkyl groups, cycloalkyl groups, aryl groups, and aralkyl groups, which are described above for $R^1$, $R^2$, $R^3$, and $R^4$ in general formula (2). In addition, substituents which may be possessed by these alkyl groups, cycloalkyl groups, aryl groups, and aralkyl groups include the alkyl groups, cycloalkyl groups, aryl groups, aralkyl groups, alkoxy groups, cycloalkyloxy groups, aryloxy groups, aralkyloxy groups, heterocyclic groups, halogen atoms, silyl groups, substituted amino groups, and optionally protected hydroxy groups, which are described above for $R^1$, $R^2$, $R^3$, and $R^4$ in general formula (2), and the like.

More preferred tridentate aminodiphosphine ligands are those represented by the following general formula (4):

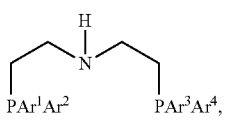

(4)

wherein $Ar^1$, $Ar^2$, $Ar^3$, and $Ar^4$, which may be the same or different, each represent an aryl group or an aromatic heterocyclic group, and the aryl group and the aromatic heterocyclic group are optionally substituted.

Examples of the aryl group and the aromatic heterocyclic group in general formula (4) include the aryl groups which are described above for $R^1$, $R^2$, $R^3$, and $R^4$ in general formula (2), and the aromatic heterocyclic groups described for the heterocyclic groups, and the like. In addition, substituents which may be possessed by these aryl groups and aromatic heterocyclic groups include the alkyl groups, cycloalkyl groups, aryl groups, aralkyl groups, alkoxy groups, cycloalkyloxy groups, aryloxy groups, aralkyloxy groups, halogen atoms, silyl groups, heterocyclic groups, substituted amino groups, and optionally protected hydroxy groups, which are described above for $R^1$, $R^2$, $R^3$, and $R^4$ in general formula (2), and the like.

A further preferred tridentate aminodiphosphine ligand is that represented by the following formula (5):

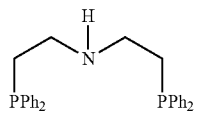

(5)

Note that, depending on the substituents on $Q^1$ and $Q^2$ and depending on $R^1$ to $R^8$, the tridentate aminodiphosphine ligand represented by general formula (2) or (3) can be used in the form of an enantiomer as a ligand of the ruthenium carbonyl complex represented by general formula (1).

In the present invention, a ruthenium compound serving as a starting material for producing the ruthenium carbonyl complex is not particularly limited, and examples thereof include inorganic ruthenium compounds such as $RuCl_3$ hydrate, $RuBr_3$ hydrate, and $RuI_3$ hydrate, $RuCl_2(DMSO)_4$, $[Ru(cod)Cl_2]n$, $[Ru(nbd)Cl_2]n$, $(cod)Ru(2-methallyl)_2$, $[Ru(benzene)Cl_2]_2$, $[Ru(benzene)Br_2]_2$, $[Ru(benzene)I_2]_2$, $[Ru(p-cymene)Cl_2]_2$, $[Ru(p-cymene)Br_2]_2$, $[Ru(p-cymene)I_2]_2$, $[Ru(mesitylene)Cl_2]_2$, $[Ru(mesitylene)Br_2]_2$, $[Ru(mesitylene)I_2]_2$, $[Ru(hexamethylbenzene))Cl_2]_2$, $[Ru(hexamethylbenzene)Br_2]_2$, $[Ru(hexamethylbenzene)I_2]_2$, $RuCl_2(PPh_3)_3$, $RuBr_2(PPh_3)_3$, $RuI_2(PPh_3)_3$, $RuH_4(PPh_3)_3$, $RuClH(PPh_3)_3$, $RuH(OAc)(PPh_3)_3$, $RuH_2(PPh_3)_4$, and the like. In the examples, DMSO represents dimethyl sulfoxide, cod represents 1,5-cyclooctadiene, nbd represents norbornadiene, and Ph represents a phenyl group.

The ruthenium carbonyl complex represented by general formula (1) can be easily produced from the tridentate aminodiphosphine ligand and the ruthenium carbonyl complex serving as a precursor. Alternatively, a commercially produced ruthenium carbonyl complex represented by general formula (1) can be purchased.

The tridentate aminodiphosphine ligand can be produced easily by reacting a bis(substituted alkyl)amine having leaving groups with a phosphide compound of an alkali metal such as lithium, sodium, or potassium.

The ruthenium carbonyl complex serving as the precursor can be obtained, for example, by the method described in Inorg. Synth, 1974, 15, 45 or the like. The ruthenium carbonyl complex of the present invention having a tridentate aminodiphosphine ligand can be formed by reacting the obtained ruthenium carbonyl complex serving as a precursor with a tridentate aminodiphosphine ligand.

For example, the ruthenium carbonyl complex represented by general formula (1) can be produced by reacting a tridentate aminodiphosphine ligand L represented by general formula (2) with $RuXY(CO)(P(Ar^5)_3)_3$, wherein $Ar^5$s, which may be the same or different, each represent an optionally substituted aryl group. The aryl groups serving as $Ar^5$s and substituents thereof include the same aryl groups and substituents as described above. Each $Ar^5$ is preferably a phenyl group optionally having a substituent such as an alkyl group, and is particularly preferably a phenyl group.

In addition, a ruthenium carbonyl complex represented by general formula (1) in which X is $BH_4^-$ can be produced by reacting a ruthenium carbonyl complex in which X is a chlorine ion with a borohydride compound, such as $NaBH_4$.

Stereoisomers may exist for the thus produced complex depending on the coordination mode and conformation of the ligands. However, the complex used for the reaction may be a mixture of these stereoisomers or a pure single isomer.

Moreover, a ruthenium carbonyl hydride borohydride complex in which a tridentate aminodiphosphine ligand exists, X=H⁻ (hydride), and Y=$BH_4^-$ can be obtained, for example, according to the method described in J. Am. Chem. Soc. 2005, 127, 516. These complexes are relatively stable, and easy to handle.

A preferred example of the complex is a complex represented by the following general formula (8):

$$RuHCl(CO)(L) \quad (8)$$

wherein (L) represents the above-described tridentate aminodiphosphine represented by general formula (5).

This complex can be produced easily by stirring the tridentate aminodiphosphine ligand L represented by general formula (5) and $RuClH(CO)(PPh_3)_3$ in a suitable solvent.

Another preferred example of the complex is a complex represented by the following general formula (9):

$$RuH(BH_4)(CO)(L) \quad (9),$$

wherein (L) represents the above-described tridentate aminodiphosphine represented by general formula (5).

This complex can be produced easily by stirring the ruthenium carbonyl complex represented by general formula (8) and a borohydride compound such as $NaBH_4$ in a suitable solvent.

A reduction method of the present invention is a method shown in the following Scheme (A) conducted by using the ruthenium complex represented by general formula (1) and hydrogen gas.

Scheme (A)

Hal—[benzene ring with $CO_2R^{Z1}$ and $(R^{Z2})_n$] ⟶ Hal—[benzene ring with $CH_2OH$ and $(R^{Z2})_n$]

(6) → (7)

Each of the groups in the halogenobenzoic acid ester and alcohol compound represented by general formulae (6) and (7) will be described.

$R^{Z1}$ may be an alkyl group having 1 to 4 carbon atoms such as a methyl group, an ethyl group, a propyl group, or a butyl group. $R^{Z1}$ is preferably a methyl group.

Each $R^{Z2}$ may be an alkyl group having 1 to 4 carbon atoms such as a methyl group, an ethyl group, a propyl group, or a butyl group; a halogen atom such as a fluorine atom, a chlorine atom, a bromine atom, or an iodine atom; or the like. $R^{Z2}$ is preferably a halogen atom, and particularly preferably a chlorine atom or a bromine atom. Moreover, each $R^{Z2}$ is preferably the same halogen atom as the Hal described later. In addition, any adjacent two $R^{Z2}$s may form a ring. The ring formed includes a benzene ring, a pyrrole ring, a pyridine ring, a pyrazine ring, a pyrimidine ring, a furan ring, a thiophene ring, and the like.

n represents 0 to 4. n preferably represents 0 or 1, and more preferably 0.

The halogen atom represented by Hal includes a fluorine atom, a chlorine atom, a bromine atom, and an iodine atom. Of these halogen atoms, a chlorine atom and a bromine atom are preferable. Moreover, the substitution position of the Hal in general formulae (6) and (7) is preferably para to the alkoxycarbonyl group and the hydroxymethyl group.

When the general formulae (6) and (7) are represented by $A-CO_2R^{Z1}$ and $A-CH_2OH$, respectively, groups of atoms preferable as A include 4-bromophenyl, 2-bromophenyl, 2,5-dibromophenyl, and 2-chlorophenyl groups.

In the reduction method of the present invention, an aromatic hydrocarbon is used as a solvent. The solvent used include toluene, xylene, mesitylene, ethylbenzene, cumene, cymene, and the like, but is not limited thereto. Of these solvents, toluene, xylene, and mesitylene are preferable.

In general, the amount of the catalyst used is as follows. Specifically, the molar ratio of the ruthenium metal to the substrate to be hydrogenated is in a range from 0.0001% by mole to 10% by mole and preferably from 0.005% by mole to 5% by mole, although the ratio varies depending on the substrate to be hydrogenated, the reaction conditions, the kind of catalyst, and the like. In the method of the present invention, the reaction temperature for carrying out the hydrogenation reduction is 0° C. to 180° C. and preferably 0° C. to 120° C. If the reaction temperature is too low, a large amount of the raw material may remain unreacted in some cases. Meanwhile, if the reaction temperature is too high, decomposition of the raw material, the catalyst, and the like may occur in some cases. Hence, such temperatures are not preferable. In the present invention, the hydrogen pressure for carrying out the reduction with hydrogen is 0.1 MPa to 10 MPa, and preferably 3 MPa to 6 MPa. In addition, the reaction time is 30 minutes to 72 hours, and preferably 2 hours to 48 hours. With such a reaction time, a sufficiently high raw material conversion can be achieved.

After completion of the reaction, the target alcohol can be obtained by one or a suitable combination of commonly employed purification methods such as extraction, filtration, crystallization, distillation, various chromatographic methods, and the like.

EXAMPLES

The present invention will be described in detail based on the Examples below. However, the present invention is not limited to these Examples in any way.

In the examples, the following analytical instruments were used.
Nuclear magnetic resonance spectroscopy (NMR): MERCURY300-C/H (Varian Inc.)
Mass spectrometry (MS): LCMS-IT-TOF (Shimadzu Corp.)
Gas chromatography (GC): GC-14A (Shimadzu Corp.)
GC: capillary InertCap
Injection temperature: 220° C., detection temperature: 250° C. 50° C. (0 minutes)-(5° C./min)-150° C.-(10° C./min)-250° C. (5 minutes)

In the following examples, the "conversion" represents the molar fraction of an alkoxycarbonyl group reduced to a hydroxymethyl group irrespective of the occurrence of the dehalogenation, and the "selectivity" represents the molar fraction of a product which underwent reduction to a hydroxymethyl group but no dehalogenation.

Complex 1 used in examples was obtained from Takasago International Corporation. Complex 2 and Complex 3 were produced in the following Reference Examples 1 and 2.

Complex 1:

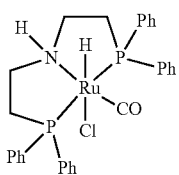

complex 1

Ruthenium Carbonyl Complexes 2 and 3 were produced based on the following reaction formulae according to the description in Organometallics 2011, 30, 3479.

Reference Example 1

Production of Ruthenium Carbonyl Complex 2

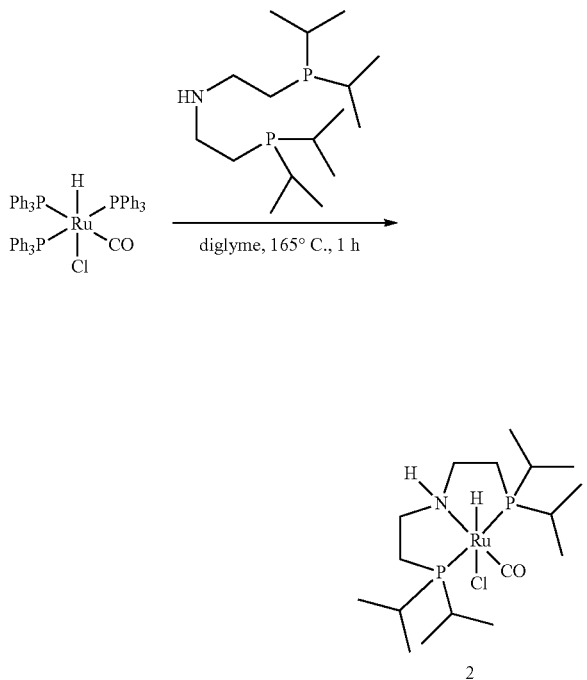

Under nitrogen stream, 329 mg (1.07 mmol) of the aminodiphosphine and 922 mg (0.956 mmol) of the ruthenium carbonyl complex shown in the reaction formula were added to a 20-ml Schlenk tube, suspended in 3 ml of diglyme, and then heated at 165° C. for 1 hour. The reaction liquid was cooled to −15° C., and the obtained crystals were separated by filtration. The crystals were washed with diethyl ether, and dried under reduced pressure. Thus, 180 mg (0.39 mmol) of Ruthenium Carbonyl Complex 2 shown in the reaction formula was obtained. $^1$H-NMR (300 MHz CD$_2$Cl$_2$): δ=−16.30 (t, J=18.0 Hz, 1H), 1.01-1.49 (m, 24H), 1.72-1.84 (m, 4H), 2.20-2.36 (m, 4H), 2.62-2.70 (m, 2H), 3.15-3.33 (m, 2H), 3.42 (bs, 1H)

$^{31}$P-NMR (121.5 MHz CD$_2$Cl$_2$): δ=75.1 (s)

HRMS (ESI): m/z calcd for C$_{17}$H$_{38}$NOP$_2$ClRu [M]$^+$ 471.1155; m/z found 471.1133.

Reference Example 2

Production of Ruthenium Carbonyl Complex 3

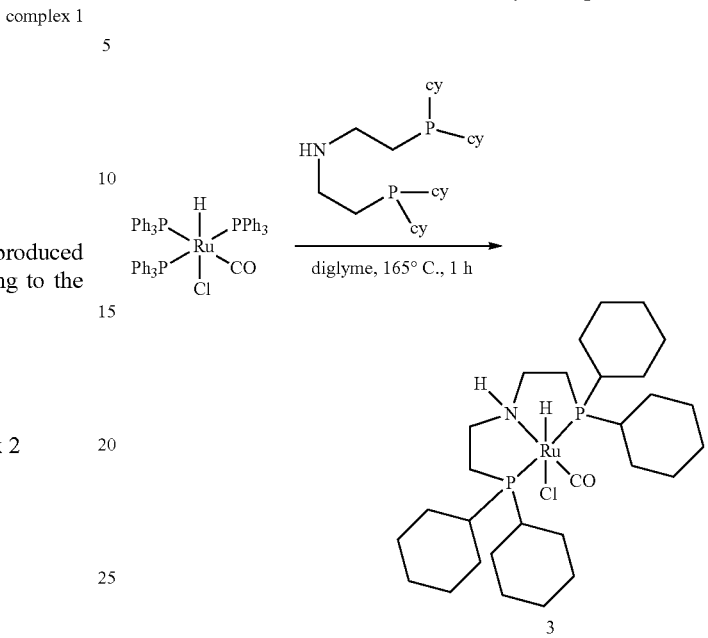

Under nitrogen stream, 706 mg (1.52 mmol) of the aminodiphosphine and 1320 mg (1.37 mmol) of the ruthenium carbonyl complex shown in the reaction formula were added to a 20-ml Schlenk tube, suspended in 4.3 ml of diglyme, and then heated at 165° C. for 1 hour. The reaction liquid was cooled to 0° C., and the obtained crystals were separated by filtration. The crystals were washed with diethyl ether, and dried under reduced pressure. Thus, 581 mg (0.92 mmol) of Ruthenium Carbonyl Complex 3 shown in the reaction formula was obtained. $^1$H-NMR (300 MHz CD$_2$Cl$_2$): δ=−16.37 (t, J=18.0 Hz, 1H), 1.25-2.02 (m, 50H), 2.20-2.40 (m, 8H), 3.19-3.25 (m, 2H), 3.50-3.52 (m, 2H)

$^{31}$P-NMR (121.5 MHz CD$_2$Cl$_2$): δ=52.8 (d, J=14 Hz)

HRMS (ESI): m/z calcd for C$_{29}$H$_{54}$NOP$_2$ClRu [M]$^+$ 631.2407; m/z found 631.2427.

Example 1

Reduction of Methyl p-Bromobenzoate (Toluene Solvent)

To a 100 ml stainless steel autoclave, 6.0 mg (0.01 mmol) of complex 1, 430 mg (2 mmol) of methyl p-bromobenzoate, and 57 mg (0.5 mmol) of KO$^t$Bu were introduced, and the autoclave was purged with nitrogen. Then, 2.0 ml of toluene was added thereto. Subsequently, hydrogen was introduced to a pressure of 5.0 MPa, followed by stirring at 80° C. for 16 hours. After cooling to room temperature, the reaction product was analyzed by GC. The conversion was 98%, the selectivity was 95%, and methyl benzoate (debrominated product) was 1%.

Comparative Example 1

Reduction of Methyl p-Bromobenzoate (Methanol Solvent)

To a 100 ml stainless steel autoclave, 6.0 mg (0.01 mmol) of complex 1 and 430 mg (2 mmol) of methyl p-bromobenzoate were added, and the autoclave was purged with nitrogen. Then, 0.5 ml (0.5 mmol) of 1 N MeONa and 1.5 ml of methanol were added thereto. Subsequently, hydrogen was introduced to a pressure of 5.0 MPa, followed by stirring at 80° C. for 16 hours. After cooling to room temperature, the reaction product was analyzed by GC. Merely dibromination of 31% of the substrate occurred which resulted in conversion to methyl benzoate (debrominated product), and p-bromobenzyl alcohol was not detected.

When the solvent was replaced with methanol, the target product was not obtained at all.

Examples 2 to 12

Reduction of Methyl Halogenobenzoates

Examples 2 to 12 were conducted in the same procedure as in Example 1 by employing the same solvent, amount of the solvent, kind of the base, amount of the base used, reaction temperature, reaction time, and hydrogen pressure as those in Example 1, except that the methyl halogenobenzoate used as the substrate and the complex used as the catalyst were changed. Table below 1 shows the results.

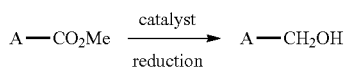

TABLE 1

| Example | Complex (% by mole) | A | Conversion | Selectivity |
|---|---|---|---|---|
| 2 | 2 (0.2% by mole) | 4-Bromophenyl | 100% | 100% |
| 3 | 3 (0.2% by mole) | 4-Bromophenyl | 93% | 88% |
| 4 | 1 (0.2% by mole) | 2-bromophenyl | 43% | 43% |
| 5 | 2 (0.2% by mole) | 2-bromophenyl | 100% | 97% |
| 6 | 3 (0.2% by mole) | 2-bromophenyl | 61% | 58% |
| 7 | 1 (0.1% by mole) | 2,5-dibromophenyl | 100% | 94% |
| 8 | 2 (0.1% by mole) | 2,5-dibromophenyl | 100% | 93% |
| 9 | 3 (0.1% by mole) | 2,5-dibromophenyl | 100% | 92% |
| 10 | 1 (0.05% by mole) | 4-chlorophenyl | 100% | 96% |
| 11 | 2 (0.05% by mole) | 4-chlorophenyl | 100% | 100% |
| 12 | 3 (0.05% by mole) | 4-chlorophenyl | 100% | 100% |

The invention claimed is:

1. A reduction method, in which dehalogenation is inhibited, the method comprising reducing a halogenobenzoic acid ester in an aromatic hydrocarbon solvent in the presence of a ruthenium complex to thereby produce an alcohol compound, the ruthenium complex being represented by the following general formula (1):

RuXY(CO)(L)   (1), wherein X and Y, which may be the same or different, each represent a monovalent anionic ligand, and L represents a tridentate aminodiphosphine ligand represented by the following general formula (2):

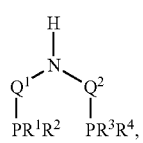   (2)

wherein $R^1$, $R^2$, $R^3$, and $R^4$, which may be the same or different, each represent a hydrogen atom, an alkyl group, a cycloalkyl group, an aryl group, an aralkyl group, an alkoxy group, a cycloalkyloxy group, an aryloxy group, an aralkyloxy group, a heterocyclic group, or a substituted amino group, each of the pair of $R^1$ and $R^2$ and the pair of $R^3$ and $R^4$ may be bonded to each other to form a ring together with the corresponding adjacent phosphorus atom, and the alkyl group, the cycloalkyl group, the aryl group, the aralkyl group, the alkoxy group, the cycloalkyloxy group, the aryloxy group, the aralkyloxy group, and the heterocyclic group are optionally substituted, and $Q^1$ and $Q^2$, which may be the same or different, each represent an optionally substituted divalent alkylene group, an optionally substituted divalent cycloalkylene group, or an optionally substituted divalent aralkylene group, the halogenobenzoic acid ester being represented by the following general formula (6):

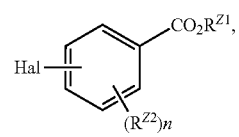   (6)

wherein $R^{Z1}$ represents an alkyl group having 1 to 4 carbon atoms, each $R^{Z2}$ represents an alkyl group having 1 to 4 carbon atoms or a halogen atom, or any adjacent two $R^{Z2}$s may form a ring, Hal represents a halogen atom, and n represents 0 to 4, the alcohol compound being represented by the following general formula (7):

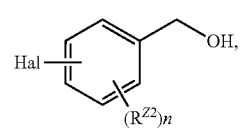   (7)

wherein each $R^{Z2}$ represents an alkyl group having 1 to 4 carbon atoms or a halogen atom, or any adjacent two $R^{Z2}$s may form a ring, Hal represents a halogen atom, and n represents 0 to 4.

2. The reduction method according to claim 1, wherein the substitution position of the Hal in general formulae (6) and (7) is para to the alkoxycarbonyl group and the hydroxymethyl group.

3. The reduction method according to claim 1, wherein the aromatic hydrocarbon solvent is selected from toluene, xylene, and mesitylene.

4. The reduction method according to claim 2, wherein the aromatic hydrocarbon solvent is selected from toluene, xylene, and mesitylene.

* * * * *